(12) United States Patent
Feulner et al.

(10) Patent No.: US 8,407,267 B2
(45) Date of Patent: Mar. 26, 2013

(54) APPARATUS, METHOD, SYSTEM AND COMPUTER-READABLE MEDIUM FOR STORING AND MANAGING IMAGE DATA

(75) Inventors: Johannes Feulner, Erlangen (DE); Shaohua Kevin Zhou, Plainsboro, NJ (US)

(73) Assignee: Siemens Aktiengesellschaft, Munich (DE)

( * ) Notice: Subject to any disclaimer, the term of this patent is extended or adjusted under 35 U.S.C. 154(b) by 359 days.

(21) Appl. No.: 12/554,436

(22) Filed: Sep. 4, 2009

(65) Prior Publication Data

US 2010/0205142 A1 Aug. 12, 2010

(30) Foreign Application Priority Data

Feb. 6, 2009 (EP) .................................... 09001672

(51) Int. Cl.
*G06F 17/30* (2006.01)
(52) U.S. Cl. .......................... 707/915; 382/131; 707/602
(58) Field of Classification Search .................. 606/130; 707/915, 602; 382/131
See application file for complete search history.

(56) References Cited

U.S. PATENT DOCUMENTS

| | | | | |
|---|---|---|---|---|
| 5,056,146 A * | 10/1991 | Nishide | ...... | 382/131 |
| 5,671,157 A * | 9/1997 | Saito | ...... | 345/419 |
| 5,835,693 A * | 11/1998 | Lynch et al. | ...... | 345/473 |
| 5,951,571 A * | 9/1999 | Audette | ...... | 606/130 |
| 7,466,849 B2 * | 12/2008 | Haider et al. | ...... | 382/128 |
| 7,995,821 B2 * | 8/2011 | Nakamura | ...... | 382/128 |
| 2002/0071677 A1 * | 6/2002 | Sumanaweera | ...... | 396/429 |
| 2002/0184238 A1 * | 12/2002 | Chylla | ...... | 707/104.1 |
| 2003/0013951 A1 * | 1/2003 | Stefanescu et al. | ...... | 600/407 |
| 2004/0205461 A1 * | 10/2004 | Kaufman et al. | ...... | 715/500 |
| 2005/0168474 A1 * | 8/2005 | Truyen | ...... | 345/581 |
| 2009/0226062 A1 * | 9/2009 | Nakamura | ...... | 382/128 |
| 2009/0226065 A1 * | 9/2009 | Chen | ...... | 382/131 |
| 2009/0279753 A1 * | 11/2009 | Sakaida | ...... | 382/128 |

OTHER PUBLICATIONS

Rosset et al., Journal of Digital Imaging, vol. 17, No. 3 Sep. 2004: pp. 205-216.*
"Beyond Bags of Features: Spatial Pyramid Matching for Recognizing Natural Scene Categories," Lazebnik et al, Computer Vision and Pattern Recognition, 2006 IEEE Computer Society Conference, pp. 2169-2178.
"Real Time Image Recognition of Body Parts Scanned in Computed Tomography Data Sets," Dicken et al, $22^{nd}$ International Congress on Computer Assisted Radiology and Surgery, (2008).

* cited by examiner

*Primary Examiner* — Cheyne Ly
(74) *Attorney, Agent, or Firm* — Schiff Hardin LLP

(57) ABSTRACT

An apparatus, method, system and computer-readable medium store and manage image data with automatic labeling of image data corresponding to body slices, such as obtained by a computed tomography scanner. The labels include a body coordinate value along the body axis. The respective body coordinate value can be determined by comparing received image data sets with reference data sets with known attached coordinate values utilizing pattern recognition techniques. Applications include medical image data management in hospitals or operating and providing medical networks. Queries for images that include particular body regions are processed more efficiently. This results in less local memory required and narrower bandwidth resources of transmission networks.

16 Claims, 6 Drawing Sheets

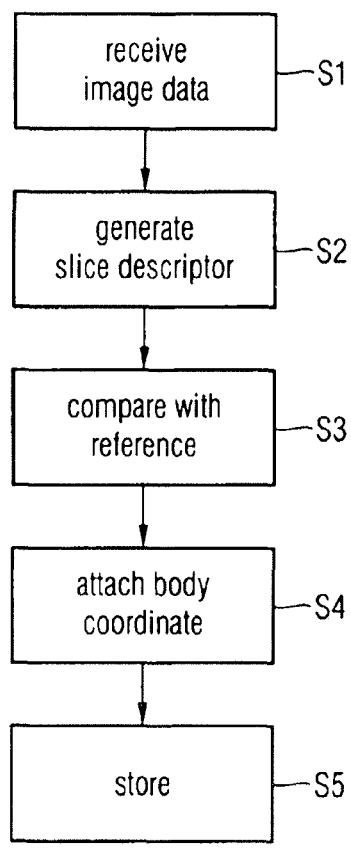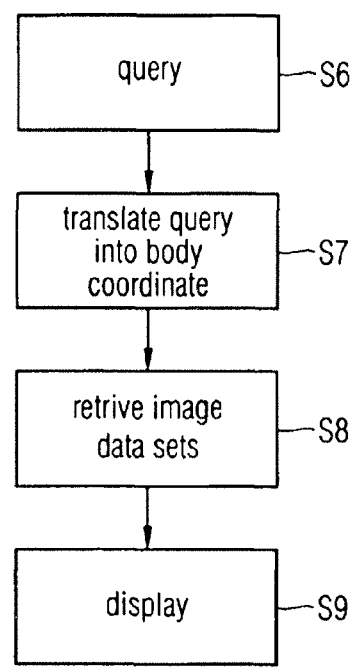

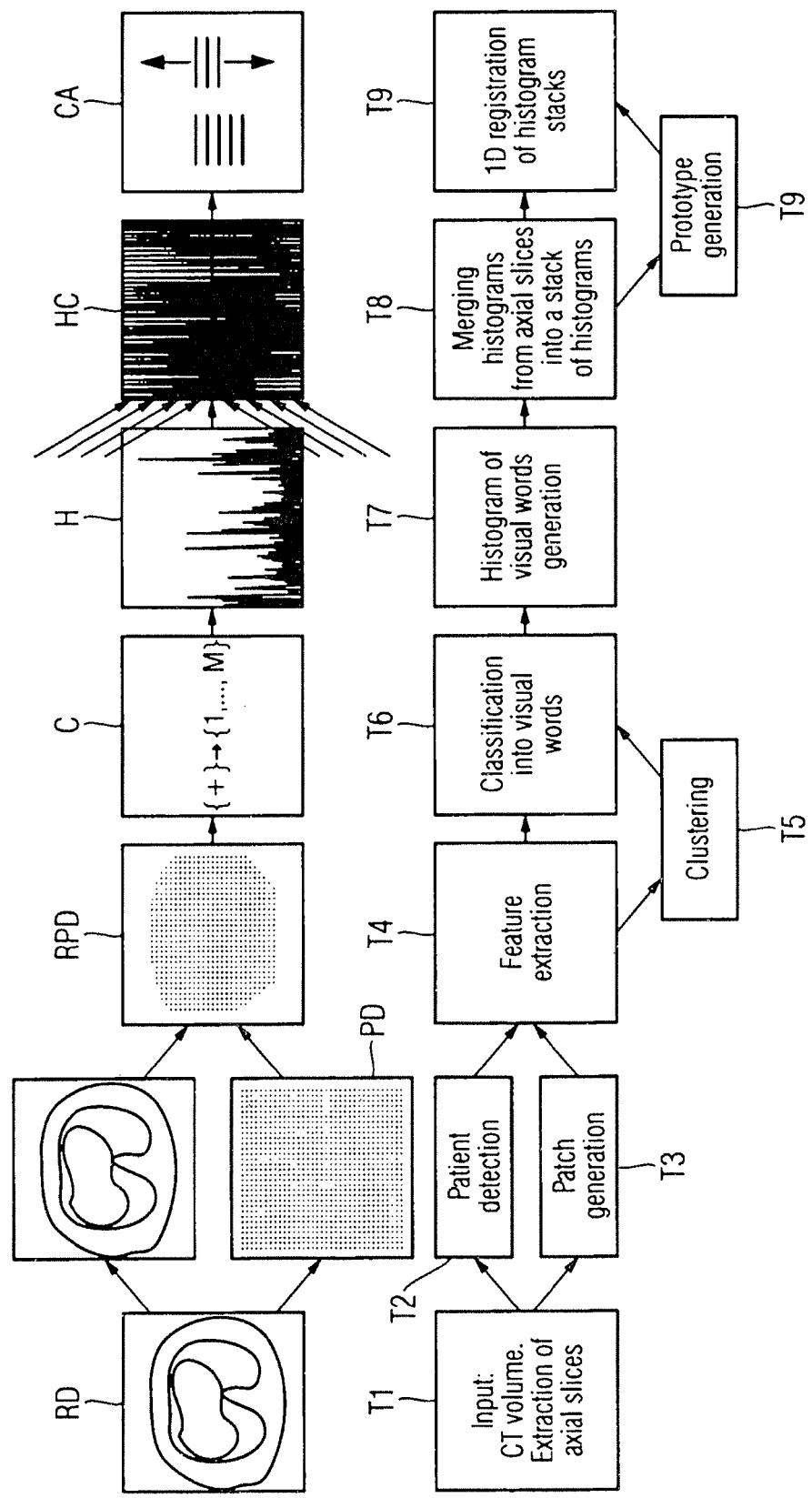

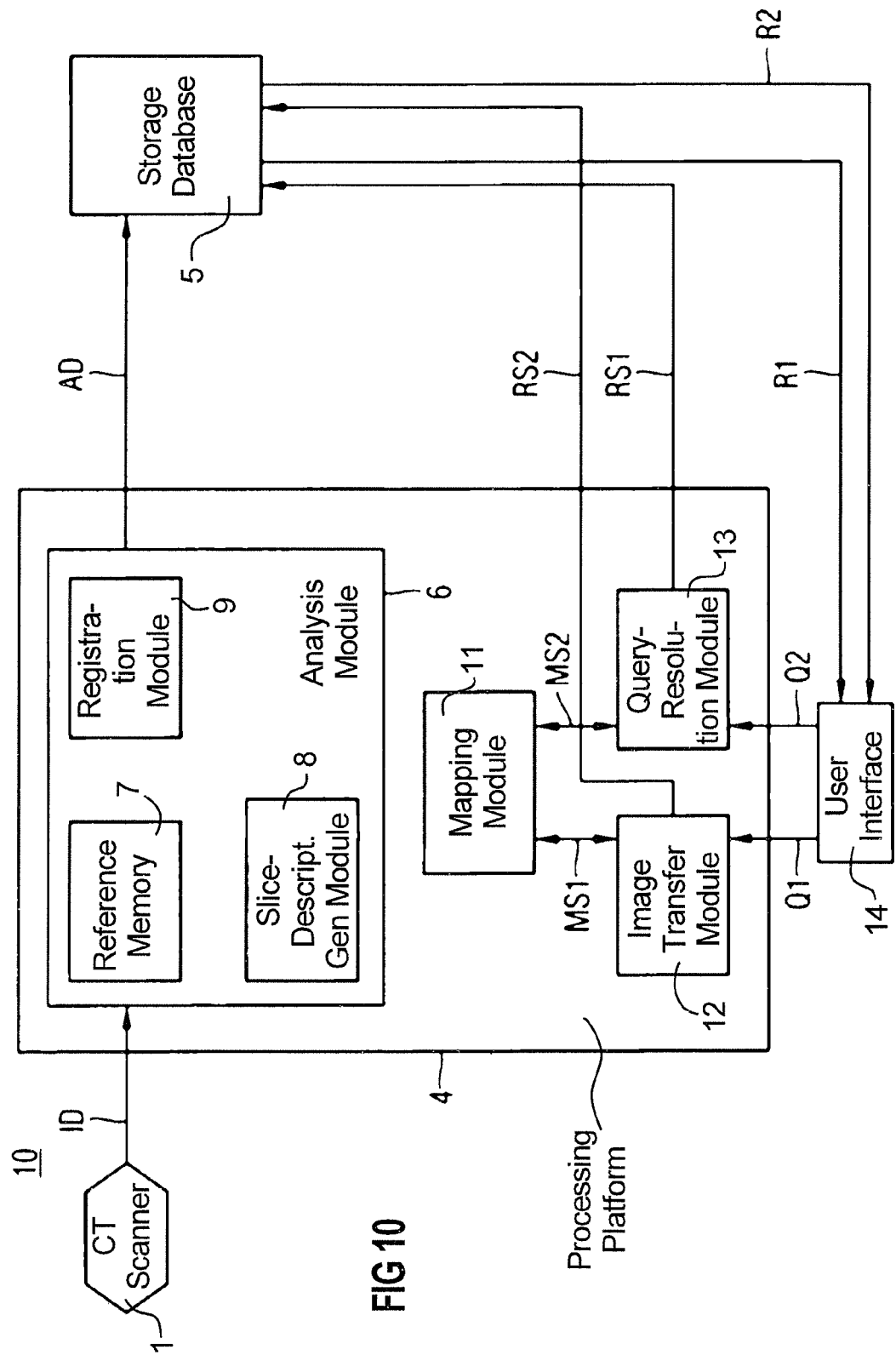

APPARATUS, METHOD, SYSTEM AND COMPUTER-READABLE MEDIUM FOR STORING AND MANAGING IMAGE DATA

BACKGROUND OF THE INVENTION

Computed tomography is used, in particular in hospitals for generating volume images of a patient's body. Usually, a variety of body slices is imaged and stored in databases. Such databases need to store large amounts of image data. If a physician needs to check a patient's therapy or assess the medical condition of a patient, he or she has to download the relevant volume images. However, often only images referring to a particular body region are relevant for assessing a medical treatment or making a diagnosis. Conventionally, the physician has to browse through the entire set of volume images of a patient's body in order to allocate the body region of interest in terms of a partial volume image. A transfer of those large amounts of data, for example, to a local computer, requires a considerable amount of transmission bandwidth and local memory. Further, transferring the entire image data of a patient's body takes a lot of time.

Therefore, medical image databases have been supplemented according to the DICOM standard. This standard involves attaching a data field entitled "body part examined" to the volume image data. The field "body part examined" refers to one of a plurality of predetermined body regions, as for example "lung", "hand", or "thorax". However, this labeling tends to be imprecise because the examined body regions are only referred to qualitatively, and all image slices corresponding to one volume carry the same "body part examined" flag.

Therefore, it may be desirable to provide an improved method or apparatus for managing and storing data, as for example medical image data.

SUMMARY OF THE INVENTION

In accordance with the invention, an apparatus for storing an image data set, wherein the image data set, for example corresponds to a computed tomography scan of a slice of a body with respect to a body axis has a memory device operable to store a plurality of reference slice description data. The apparatus further comprises a processing platform operable to assign slice description data to the image data set according to a predetermined feature extraction technique. The processing platform is operable to attach a body coordinate value to the body image data set as a function of a comparison result between the slice description data and the reference slice description data. The body coordinate value refers to a position along the body axis. Additionally, the apparatus has a storage device operable to store the image data set and the attached body coordinate value.

The invention also encompasses a method for storing image data, including providing a plurality of image data sets, wherein an image data set corresponds to a computer tomography scan of a slice of a body with respect to a body axis. The method includes retrieving at least one image data set corresponding to a slice of a body, assigning slice description data to the image data set, comparing the slice description data with reference slice description data for determining a body coordinate value referring to a position along the body axis, attaching the body coordinate value to the image data set, and storing the image data set and the attached body coordinate value.

The invention also encompasses a system for providing body image data, having a computed tomography scanner to scan a body and to provide at least one body image data set corresponding to a slice of the body with respect to a body axis. The system includes a processing platform operable to retrieve the at least one body image data set, to assign slice description data to the body image data according to a predetermined feature extraction technique, and to attach a body coordinate value to the body image data set as a function of a comparison result between the slice description data and reference slice description data. The system also includes a memory device operable to store the body image data set and the attached body coordinate value.

The invention also encompasses a computer-readable medium having computer-executable instructions for execution by a processing system. The computer-executable instructions for managing and storing an image data set, the image set corresponding to a computed tomography scan of a slice of a body with respect to a body axis, include instructions that assign slice description data to the image data according to a predetermined feature extraction technique, instructions to attach a body coordinate value to the body image data set as a function of a comparison result between the slice description data and reference slice description data wherein the body coordinate value refers to a position along the body axis. The instructions also comprise instructions to store the image data set and the attached body coordinate value.

BRIEF DESCRIPTION OF THE DRAWINGS

FIG. 3 shows an illustration of a flow chart according to a first aspect of a method for storing and managing image data.

FIG. 4 shows an illustration of a flow chart according to a second aspect of a method for storing and managing image data.

FIG. 9 shows a schematic illustration of various aspects of a method for storing and managing image data.

FIG. 10 shows a schematic illustration of an embodiment of a system for storing and managing image data.

DESCRIPTION OF THE PREFERRED EMBODIMENTS

Figure 1:
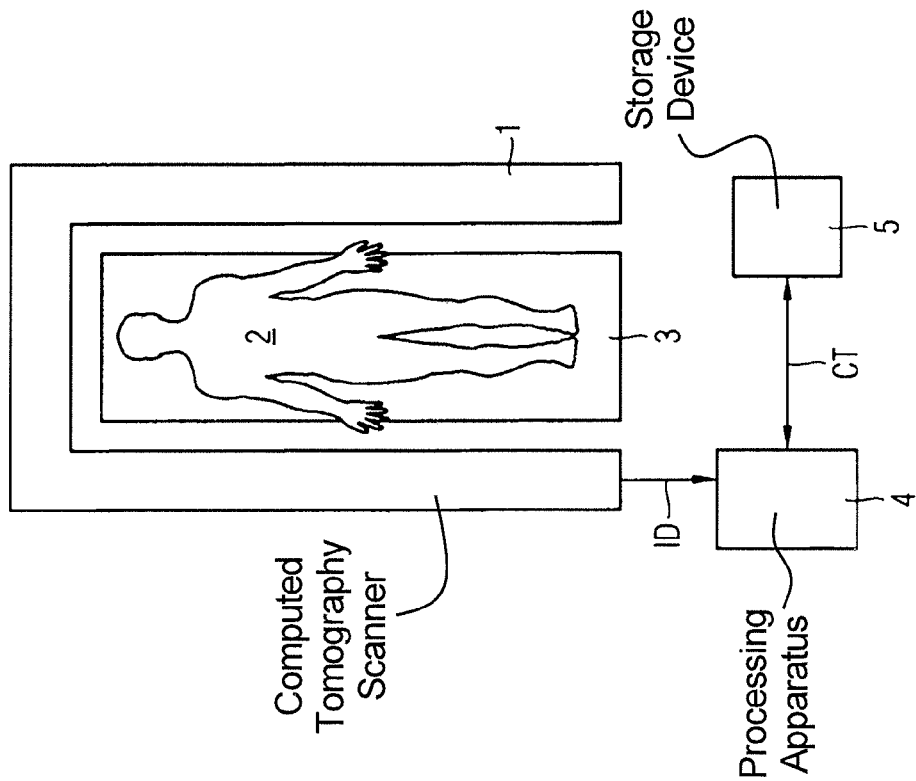
FIG. 1 shows a schematic illustration of an embodiment of an apparatus for storing image data.

The before mentioned summarized aspects of an apparatus, a method, a system and a computer-readable medium for storing and/or managing image data can be supplemented by a variety of additional aspects.

For example, the processing platform may be further operable to allocate image data portions of the image data set. An image data portion is associated to a patch of the slice of the body, wherein a number of patches covers the slice of the body. The processing platform may be further operable to classify each image data portion into a visual word class for a plurality of predetermined visual word classes.

For example, one may contemplate a grating over the slice of a body where regular patches such as rectangular forms or squares cover the entire slice. It is also conceivable that each patch comprises a certain number of pixels obtained through a computed tomography scan. By classifying the image data portions, for example corresponding to the patches, one may construct characteristic data of a respective image data set as a function of the assignment to visual word classes. A visual word class may for instance refer to a certain material, such as body tissue, bone material, surrounding air, skin tissue or water.

According to one aspect of the apparatus, the processing platform is further operable to generate a histogram of the classified visual word classes and to calculate a similarity measure between the histogram and the plurality of predetermined reference histograms. The bins of a respective histogram may refer to a visual word class, and the number of entries, i.e. the number of image data portions classified to a respective visual word class, can serve as a footprint of the image data set. A similarity measure, as for example a Euclidean distance or any other geometric norm between histogram vectors of the image data set and a respective reference image data set can facilitate the assignment or attachment of the body coordinate value.

As an example, each predetermined reference histogram can be associated to a reference body coordinate value. Hence, by determining the most similar reference slice description data, for example comprising a histogram of classified visual word classes, the body coordinate value of the reference image data set can be assigned to the image data set processed in the apparatus or processing platform.

According to an aspect of the apparatus for storing an image data set, the processing platform is operable to allocate image data portions of the image data set, wherein an image data portion is associated to a patch of the slice of a body, wherein a plurality of patches cover the slice of a body. The processing platform is then operable to classify the image data portions into body material related image data portions as a function of a Hounsfield value of the image data portions. For example, the pixels of a CT scan can be regarded as an image portion. Then, the processing platform deletes image data portions that are unrelated to body material. This aspect has the advantage that the image data set to be processed and stored can be reduced, and it also increases the robustness because superfluous data, of the table of the CT device and the air surrounding the patient does not influence any recognition processes.

According to yet another aspect of the apparatus, the processing platform is further operable to assign a text label to the image set as a function of the attached body coordinate value. For example, the body coordinate value can be set on a normalized scale defined by a first and a second anatomical landmark along the body axis. Then, each body coordinate value can be associated with a body region described by a text label. For example, a text label "lung" may refer to a body coordinate value of 0.6.

According to an aspect of the method for storing image data, the optional method steps can be provided: dividing the slice of the body into patches, each patch having an associated image data portion, and classifying each image data portion into a visual word class of a plurality of predetermined visual word classes.

The aspect can be further supplemented by slice description data comprising a histogram of the classified visual word classes and the step of calculating a similarity measure between the histogram and a plurality of predetermined reference histograms.

The method according to another aspect with respect to assigning slice description data can include the steps of: dividing the slice of the body into patches, each patch having associated image data portions, detecting patches corresponding to body material, and deleting image data portions that do not correspond to body material. As mentioned above, these optional steps may serve to reduce the amount of data to be transferred and processed in a system operating according to aspects of the presented method.

Yet another aspect of the method for storing and/or managing image data includes:
providing a reference body;
setting a first and a second anatomical landmark along a reference body axis;
generating a plurality of reference image data sets, a reference image data set corresponding to a computer tomography scan of the slice at predetermined positions with respect to the first and second anatomical landmark of the reference body along the reference body axis;
generating reference slice description data for at least one reference image data set according to a predetermined feature extraction technique.

Hence, one may generate reference data by using a known geometry of a reference body and assign each reference image data set corresponding to a reference body slice, the actual body coordinate value on a scale that depends on at least two anatomical landmarks. As an anatomical landmark, one may contemplate about the clavicle and the pelvis, for example.

The method can also include associating at least one text label to a predetermined range of body coordinate values. For example, a certain range of coordinate values along the one-dimensional body axis can refer to certain body regions. Hence, by estimating or determining the body coordinate value, the respective image data set is characterized.

Text labels may comprise intuitive expressions or descriptions of body parts or anatomical terms.

At least one computed tomography scan can be performed for generating the multiple image data sets, wherein the slices of the body are essentially parallel to one another and essentially perpendicular to the body axis. In computed tomography, for example, a stack of slices at predetermined distances along the body axis may form a volume image of the body under consideration.

In the apparatus or system, the processing platform can be further operable to divide the slice of the body into patches, each patch having an associated image data portion, and to process the image data portions according to predetermined pattern recognition technique for classifying the image data portions into visual words. The visual words or classes may, for example, comprise particular properties of the image data portions. As an example, a visual word class may refer to portions that do not correspond to body materials. Consequently, the processing platform can be operable to delete image data portions that are classified into a visual word corresponding to non-body materials. For example, a non-body material can be the surrounding air or a table material on which the body is placed during the computer tomography scan process.

According to one aspect of the system, a query resolution device is operable to receive a query text and to match the query text to a query body coordinate value. As an example, a query can be submitted to an input device by a physician. The query text may relate to a body region of which the physician needs CT image data. By mapping the query text to query coordinate values, the particular body image data sets referring to the coordinate values or body region can be retrieved. This leads to a reduced need of local memory or transmission bandwidth for transmitting the required image data sets. The system can therefore further include a data retrieval device operable to retrieve at least one image data set having an attached body coordinate value corresponding the query body coordinate value.

In one embodiment of the system for storing and managing body image data, the computer tomography scanner, the processing platform, the memory device, the retrieval device and the query resolution device are communicatively coupled through a network infrastructure. As an example, the Internet may serve as a network infrastructure. However, other networks can be contemplated.

The computer-readable medium can be embodied as a memory device storing a computer program product. For example, a USB memory stick, floppy discs or other computer-readable memory means may be utilized. Further, the method can be implemented as a downloadable file on a network server.

Those skilled in the art are able to combine the above-described aspects of an apparatus, a method, a system and a computer-readable medium for storing and managing image data. Hence, the combinations of features or aspects illustrated in the exemplary embodiments are not to be considered as limiting the scope or spirit of this disclosure.

FIG. 1 shows an embodiment of an apparatus for storing image data. The arrangement of FIG. 1 has a computed tomography scanner 1, a processing apparatus 4, which for example can be implemented as a processing platform or a PC, being communicatively coupled to the computed tomography (CT) scanner 4, and a storage device 5 holding for example a database with CT volume data. The storage device 5 can be controlled through control signals CT by the processing platform 4. The CT scanner 1 scans, for example, the body of a patient 2 who lies on a table 3 inside the CT apparatus 1. Consequently, image data ID is transferred to the processing platform 2.

The arrangement according to FIG. 1 allows determining automatically which portion of the human body 2 is shown by CT volume images generated by the CT apparatus and stored in the storage device 5. A CT volume image comprises usually a plurality of image data sets each set corresponding to the scan of a slice of the body. For example, along the longitudinal axis of the body 2 can be defined as a body axis along which perpendicular slices of image data are generated. The processing platform 2 analyzes the image data ID, in particular image data sets corresponding to the slices of the body, and attaches labels to the data sets including a body coordinate value. The body coordinate value designates a position along the body axis and therefore relates to certain body regions if the scale of the coordinates is chosen appropriately.

Figure 2:
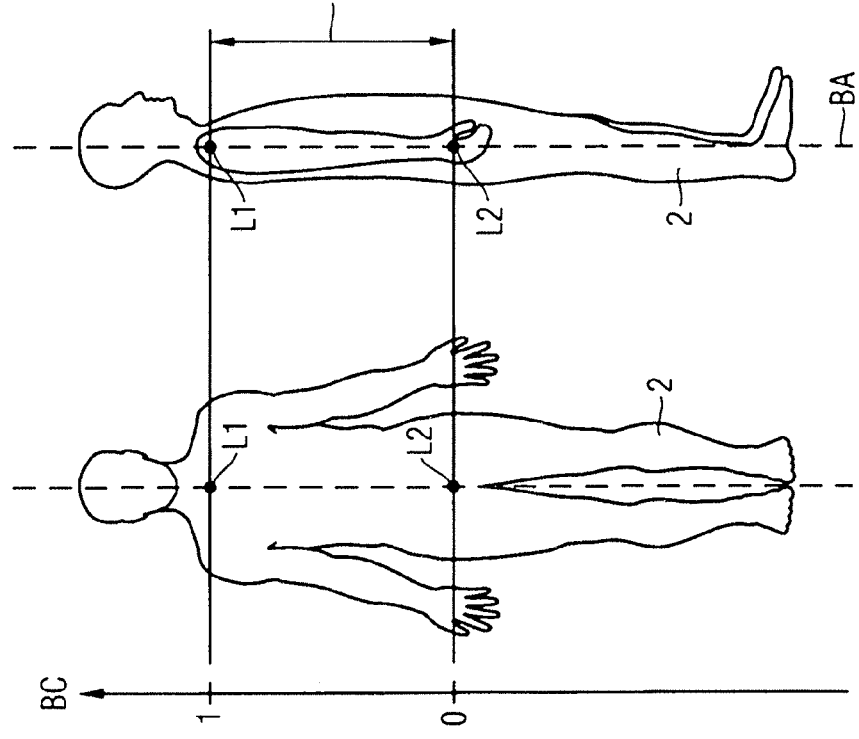
FIG. 2 shows a schematic diagram of a body for illustrating a body coordinate system.

For illustrating the possible body coordinate system, FIG. 2 shows schematic diagrams of a body, for example of a patient. In the upper section of FIG. 2, a cross-sectional view of a body 2 along its length is shown, while the lower section of FIG. 2 shows a front view or top view of a patient's body, as for example on the table 3 shown in FIG. 1. One may define a body axis BA running from the head to the feet, for example along the spine. The body axis BA is shown as a dashed line in FIG. 2. For setting a universal scale for the one-dimensional body coordinates along the axis BA, anatomic landmarks L1, L2 are defined. The first landmark point L1 corresponds to the position of the clavicle on the body axis BA. The second anatomic landmark L2 is chosen at the position of the pelvis along the body axis BA. The two anatomic landmarks L1 and L2 define a universal length UL used as a universal scale for body coordinates. For example, the body coordinate scale BC has its origin O at the pelvis position, and the body coordinate value corresponding to 1 is at the clavicle position. This is illustrated in the lower part of FIG. 2.

By defining universal body coordinates, for example according to FIG. 2, slices of the body that are generated perpendicularly to the body axis, may be assigned a respective body coordinate value. For example, a perpendicular slice in the brain region would be in the body coordinate range of 1.0 to 1.3. A typical region where image data sets corresponding to the slices including the heart are in the range between 0.5 and 1 in terms of body coordinates.

FIG. 3 and FIG. 4 show flow charts according to embodiments of the method for storing and managing respective CT image data. For example, the processing platform 4 as shown in FIG. 1 may be implemented to perform or execute the method steps illustrated in FIG. 3 or 4. Referring now to FIG. 3, in a first step S1 image data is received. CT volume image data usually comes in image data sets wherein a respective image data set corresponds to a CT scan of a slice of the body. The image data set, for example, can be a CT scan of the thorax, but may also be a CT scan of the entire body.

Next, in step S2 slice description data is generated and assigned to the respective image data set. The slice description data for example can be implemented as a feature vector for the image data set. The term slice descriptor is used synonymously.

Next, the generated slice description data or, for example, a feature vector associated to the received image data set is compared with reference slice description data in step S3. Reference slice description data may be available in a dedicated memory of the processing platform. As a result of comparing the slice description data with the reference slice description data, one obtains a best match of the received image data set with a reference data set.

In step S4, a body coordinate value is attached to the initially received image data set as a function of the best match with a reference slice description data. For example, if in the comparison step S3 it is found that the received image data set best corresponds to a reference data set as acquired for the pelvis of a reference body, a body coordinate value of 0 is attached to the image data set.

Finally, in step S5, the image data set and the attached body coordinate value is stored in a memory device. The memory device can be, for example, the database 5 as shown in FIG. 1.

By automatically attaching a body coordinate value to the image data set, handling and managing all image data sets forming the volume image of the scanned body is facilitated.

FIG. 4 shows a flow chart according to another aspect of a method for managing and retrieving desired CT image data. For example, a physician needs to examine image data referring to a certain body region of a patient. Hence, in step S6, a query is submitted to the processing platform 4 as shown in FIG. 1. The query may comprise an anatomic expression such as hip, thorax, lung or other expressions.

In the next step S7, the submitted query expression or query text is translated into a body coordinate. For example, there can be provided a mapping table for translating a vocabulary of query expressions to body coordinate values. For example, referring back to FIG. 2, a query expression "clavicle" is translated to a body coordinate value of 1.

Next, exclusively the image data sets corresponding to body coordinate value related to the query of step S6 are retrieved from the database in step S8.

Finally, the image data can be displayed in step S9 showing the portion of the body corresponding to the query of the physician. It is an advantage that only a limited amount of data needs to be transferred and retrieved because the image data sets are labeled with body coordinate values. Hence, only image data sets corresponding to a respective range of body coordinate values matching with the query are retrieved, transferred and displayed.

Figure 5:
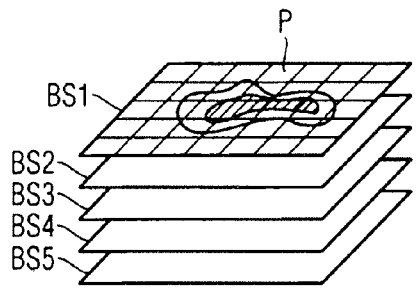
FIG. 5 shows an illustration of imaged body slices.
Figure 6:
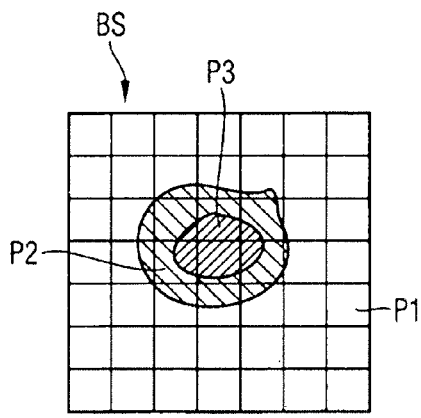
FIG. 6 shows an illustration of an embodiment of patches covering a body slice.
Figure 7:
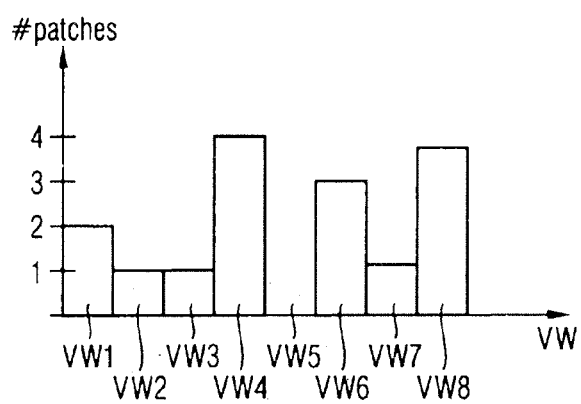
FIG. 7 shows an illustration of an embodiment of a histogram of classified patches.

The calculation of description data for image data sets corresponding to body slices is better understood referring to FIGS. 5-7. FIG. 5 shows a stack of body slices BS1, BS2, BS3, BS4, BS5 generated by a CT scanner. In order to extract image features of the respective image data set, the body slice BS1 can be divided into patches P. For example, body slice BS1 has patches P. Generally speaking, a stack of a plurality of image data sets corresponds to a volume image of a body processed in a CT scanner. For extracting image features, the patches P of the respective body slice or the image data set, respectively, can be classified into visual words.

FIG. 6 shows the body slice BS divided into regular patches arranged in a 9 by 9 matrix. Other patch geometries can be contemplated. In order to reduce the calculational effort in processing the image data sets, the patches can be classified into patches referring to body material and patches referring to non-body material, such as the body surrounding air, clothes, or the table on which the body is put for the CT scan. For example, the patches outside the patient's body can be rejected and deleted in further processing. In the example shown in FIG. 6, patch P1 is not related to body material. Patches P2 and P3, however, has image data relating to body material.

For example, each patch comprises pixels of the CT scan. The pixels are usually provided on a Hounsfield scale. Hence, a criterion for classifying a patch comprising non-body material images can be chosen such that a predetermined number of pixels associated to a patch has to be above or below a threshold value, of, for example, −600 Hounsfield units (HU). For example, all patches outside the hatched region in FIG. 6 can be classified as not relating to body material.

Next, referring now to FIG. 7, the slice descriptor or slice description data can be obtained by counting the number of patches classified into the respective visual words. A visual word usually refers to primitive patches that are used to characterize a collection of images. For example, a visual word class can be patches containing straight lines, that are easily detectable by a respective pattern recognition technique. The visual word vocabulary may include visual word classes, such as straight lines, corners, uniform patterns, holes or certain textures.

In FIG. 7, eight bins BW1-BW8 are shown. For creating the histogram all patches belonging to a slice BS are classified into a respective visual word class. The histogram shows the distribution of this classification for the respective image data set or the slice, respectively. Each body slice as shown in FIG. 5 can be characterized by a respective histogram as shown in FIG. 7. Hence, a histogram may serve as a slice descriptor. One can also refer to the histogram as a histogram vector.

Figure 8:
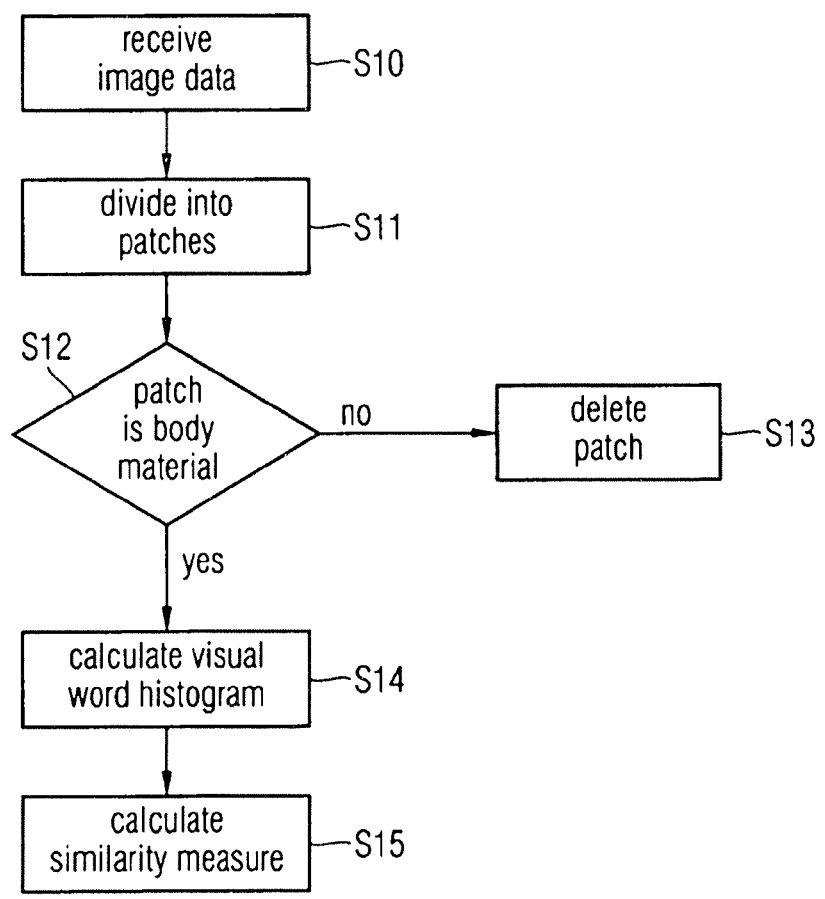
FIG. 8 shows an illustration of a flow chart according to a third aspect of a method for storing and managing image data.

FIG. 8 shows a flow chart portion for generating description data which can be implemented in the method for storing and managing image data. In particular, the flow chart of FIG. 8 refers to the generation of slice descriptors and to the comparison of such slice descriptors with reference descriptors. For example, FIG. 8 can be understood as a more detailed illustration of steps S2 and S3 as shown in FIG. 3.

First, in step S10, one receives the image data sets. This is, for example, illustrated as a stack of body slices BS1-BS5 in FIG. 5. Next, the body slices are divided into patches in step S11. Then, in step S12, it is determined whether a patch relates to body material or not. If a respective patch does not relate to body material, hence the patch refers to a region in the CT scan outside the patient's body, the patch is deleted in step S13.

If it is determined that respective patches contain image data relating to the body material, a visual word histogram is calculated in step S14. An example histogram is shown in FIG. 7.

Next, a similarity measure between the calculated visual word histogram with reference histograms is calculated in step S15. Since a reference histogram refers to a reference slice and consequently to a reference body coordinate value, the body coordinate value of the best matching reference histogram is assigned or attached, respectively, to the image data set comprising all the patches.

FIG. 9 shows schematic illustrations of aspects involved in the herewith disclosed apparatuses for storing and managing image data or processing steps implemented thereby. In the first process stage T1, an axial slice is extracted from a CT volume image. For example, image RD refers to a CT slice. Next, one may generally detect the actual patient and associate a name or patient number received image data (T2). Medical personal, for example, can tag the volume data with a respective name. Next, patches can be generated (T3), for example, on a regular grating or grid as shown in image PD. Then, in stage T4, the patches are classified and features are extracted as a function of the patch characteristics. For example, the image RPD shows only patches relating to body material while, as explained above, other patches are discarded or deleted for the further data processing.

For each patch, a feature vector, for example, can be extracted according to a predetermined feature extraction algorithm. The feature vector for a patch allows classifying the patch into a visual word. This is shown in FIG. 9 as stage T6. The classification into visual words is illustrated by image C. Histograms of visual words in stage 7 can be generated. An example histogram is shown as image H. In stage T7, each slice or body image that has an associated histogram serves as a descriptor for the image data set. Histograms can be merged to a stack of histograms similar to the stack of slices shown in FIG. 5. In stage 18, histograms are combined.

This can be illustrated as a histogram combination shown in image HC.

In order to generate the reference histograms as mentioned with respect to the foregoing aspects of the methods and apparatuses one may process training image volumes with known annotations of the pelvis and clavicle landmarks. This results in a set of prototype reference histogram stacks. In order to set the plurality of visual words forming the visual word vocabulary, one may use cluster algorithms for the feature vectors of the patches derived from the training volumes (stage T5). In stage T9, prototype or reference histograms are created wherein reference histogram has an assigned body coordinate value. This is illustrated in stage T9 as registration of the histogram stacks.

Finally, the histogram stacks are used to measure the similarity of the actual CT slice with a reference slice. The dimension of a slice may vary, however, sizes of 35 cm by 35 cm are feasible. One may choose 1000 samples or visual words.

For example, the distance d(S, T) between two slices of the respective histograms can be compared using the sum of absolute differences. This can be implemented, for example, considering the slice S and the slice T and the respective histograms $H_s$ and $H_T$:

$$d(S, T) = \sum_{i=0}^{M-1} |H_s(i) - H_T(i)|,$$

wherein M denotes the number of bins or visual word classes in the histogram.

The procedure allows to automatically determine which portion of the human body is shown in a CT body slice. This facilitates automatic labeling of the image data sets and subsequent image analysis.

FIG. 10 shows the embodiment of a system for storing and managing CT image data. System 10 includes a CT scanner 1, a processing platform 4 such as a PC or a program controlled device such as a microprocessor, a storage database 5 and a user interface 14. The CT scanner 1 delivers image data ID to the processing platform 4. The storage database 5 can be implemented as a picture archiving and communication system (PACS). The user interface 14 is, for instance, a keyboard, a touch screen device, or a speech recognition device for submitting queries Q1, Q2 to the processing platform 4. However other input means are conceivable.

In one mode of operation, for instance, the processing platform has an analysis module 6. The analysis 6 module receives image data sets ID from the CT scanner 1. A slice description generating module 8 of the analyses module 6 generates slice descriptors or slice description data sets as explicated above. In particular, based on CT scans of reference bodies, one or more reference volume images can be saved in a reference memory 7. Reference slice description data, for example comprise reference histograms, that correspond to particular body coordinate values. Analysis module 6 compares the received image data sets ID with the reference data sets or the calculated histograms of the reference histograms, respectively, and assigns the coordinate values to the slices. A registration module 9 transmits the annotated image data ID, i.e. the image data sets attached with a label comprising the body coordinate value to the storage database 5.

If the user, such as a physician, needs to evaluate CT images referring to certain body regions, he or she can submit a query Q1, Q2 to an image transfer module 12 or a query resolution module 13. For example, a query Q1 comprises the expression neck or thorax. A mapping module 11 maps a query text or query expression to respective ranges of body coordinate values. For example, a query neck is mapped to coordinate values in a range between 1.1 and 1.3. A query "leg", however, is mapped to negative body coordinate values by mapping module 11.

A transfer query Q1 results in the image transfer module 12 to allocate the relevant body coordinate range from the mapping module 11 through messages MS1. Next, the image transfer module 12 sends a request RS2 to the storage database which consequently transmits the image data sets corresponding to the body coordinate interval matching with the query Q1, for example over a network. This is illustrated as arrow R2. However, if a search query Q2 is submitted through the user interface 14, the query resolution module 13 obtains the relevant coordinate interval as a message MS2 from the mapping module 11 and requests (MS1) the transmission of the entire volume image including the queried body coordinate interval.

The disclosed aspects of apparatuses, methods and systems allow to automatically analyze image data sets acquired by CT scanners. Further, the image data sets are automatically labeled with an appropriate body coordinate value and stored. Hence, the image data and the position data in terms of the body coordinate value are stored in a database. Consequently, queries, for example by physicians, can be limited to the body region of interest, and therefore only a reduced amount of data is to be transferred and eventually analyzed. This results in a reduced amount of local memory needed, and the more efficient use of network resources in medical networks. Consequently, the image management of in particular medical data image data is performed more efficiently.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for storing an image data set comprising image data generated by a computed tomography scan of a slice of a body of a patient with respect to a body axis, said apparatus comprising:

a memory device in which reference slice description data are stored that represent a reference body other than the patient and that are organized in said memory according to reference body coordinates representing respective locations in said reference body along said body axis;

a processing platform configured to assign slice description data to the image data set according to a predetermined feature extraction technique, and to execute a comparison between the slice description data and the reference slice description data to identify highest correlating reference slice description data in said memory device, that have a highest statistical correlation to the slice description data assigned to said image data set, and to attach a reference body coordinate value to the image data set corresponding to a location along the body axis of the highest correlating reference slice description data;

a storage device in which the image data set and the attached reference body coordinate value are stored; and said processing platform being configured to receive a query for said image data set in the form of slice description data and to convert the slice description data of the query into a reference body coordinate, and being configured to retrieve the image data set from the storage device by finding the reference body coordinate value attached to the image data set said storage device that corresponds to the reference body coordinate into which the query was converted.

2. The apparatus of claim 1, wherein the processing platform is configured to allocate image data portions of the image data set respectively to a patch of the slice of the body of the patient, among a plurality of patches that cover the slice of the body of the patient, and to classify each image data portion into a visual word class, among a plurality of predetermined visual word classes that are respectively associated with said plurality of patches, and to assign said slice description data as one of said visual word classes.

3. The apparatus of claim 2, wherein the processing platform is configured to generate a histogram of the classified visual word classes, and to calculate a similarity measure between the histogram and a plurality of reference histograms respectively associated with said reference slice description data in said memory device, and to use said similarity measure as said comparison to identify said highest-correcting slice description data.

4. The apparatus of claim 2, wherein said processing platform is configured to classify the image data portions into body material-related image data portions as a function of a Hounsfield value of the image data portions, and to delete, from said storage device, image data portions in patches that are unrelated to body material.

5. A system for storing an image data set comprising:

a computed tomography device configured to implement a computed tomography scan of a body of a patient with respective to a body axis, to generate an image data set representing a slice of the body of the patient with respect to the body axis;

a memory device in which reference slice description data are stored that represent a reference body other than the patient and that are organized in said memory according to reference body coordinates representing respective locations in said reference body along said body axis;

a processing platform configured to assign slice description data to the image data set according to a predetermined feature extraction technique, and to execute a comparison between the slice description data and the reference slice description data to identify highest correcting reference slice description data in said memory device that have a highest statistical correlation to the slice description data assigned to said image data set, and to attach a reference body coordinate value to the image data set corresponding to a location along the body axis of the highest correlating reference slice description data;

a storage device in which the image data set and the attached reference body coordinate value are stored; and said processing platform being configured to receive a query for said image data set in the form of slice description data and to convert the slice description data of the query into a reference body coordinate, and being configured to retrieve the image data set from the storage device by finding the reference body coordinate value attached to the image data set into said storage device that corresponds to the reference body coordinate into which the query was converted.

6. The apparatus of claim 5, wherein the processing platform is configured to allocate image data portions of the image data set respectively to a patch of the slice of the body of the patient, among a plurality of patches that cover the slice of the body of the patient, and to classify each image data portion into a visual word class, among a plurality of predetermined visual word classes that are respectively associated with said plurality of patches, and to assign said slice description data as one of said visual word classes.

7. The apparatus of claim 6, wherein the processing platform is configured to generate a histogram of the classified visual word classes, and to calculate a similarity measure between the histogram and a plurality of reference histograms respectively associated with said reference slice description data in said memory device, and to use said similarity measure as said comparison to identify said highest correcting slice description data.

8. The apparatus of claim 6, wherein said processing platform is configured to classify the image data portions into body material-related image data portions as a function of a Hounsfield value of the image data portions, and to delete, from said storage device, image data portions in patches that are unrelated to body material.

9. An apparatus for storing an image data set comprising image data generated by a computed tomography scan of a plurality of slices of a body of a patient with respect to a body axis, said apparatus comprising:

a memory device in which reference slice description data are stored that represent a reference body other than the patient and that are organized in said memory according to reference body coordinates representing respective locations in said reference body along said body axis;

a processing platform configured to assign slice description data to respective slices in the image data set according to a predetermined feature extraction technique, and to execute a comparison between the slice description data and the reference slice description data to identify highest correlating reference slice description data in said memory device that have a highest statistical correlation to the slice description data respectively assigned to said slices in said image data set, and to attach respective reference body coordinate values to the respective slices in the image data set corresponding to locations along the body axis of the highest correlating reference slice description data;

a storage device in which the image data set and the attached reference body coordinate value are stored; and said processing platform being configured to receive a query for said image data set in the form of slice description data and to convert the slice description data of the query into a reference body coordinate, and being configured to retrieve the image data set from the storage device by finding the reference body coordinate value attached to the image data set said storage device that corresponds to the reference body coordinate into which the query was converted.

10. A method for storing an image data set comprising image data generated by a computed tomography scan of a slice of a body of a patient with respect to a body axis, said apparatus comprising:

in a memory device, storing reference slice description data that represent a reference body other than the patient and organizing said reference slice description data in said memory according to reference body coordinates representing respective locations in said reference body along said body axis;

in a processing platform, assigning slice description data to the image data set according to a predetermined feature extraction technique, and executing a comparison between the slice description data and the reference slice description data to identify highest correlating reference slice description data in said memory device that have a highest statistical correlation to the slice description data assigned to said image data set, and attaching a reference body coordinate value to the image data set corresponding to a position along the body axis of the highest correcting reference slice description data;

storing the image data set and the attached reference body coordinate value in an image storage device; and said processing platform receiving a query for said image data set in the form of slice description data and converting the slice description data of the query into a reference body coordinate, and retrieving the image data set from the storage device by finding the reference body coordinate value attached to the image data set said storage device that corresponds to the reference body coordinate into which the query was converted.

11. The method of claim 10 comprising, in the processing platform, allocating image data portions of the image data set respectively to a patch of the slice of the body of the patient, among a plurality of patches that cover the slice of the body of the patient, and classifying each image data portion into a visual word class, among a plurality of predetermined visual word classes that are respectively associated with said plurality of patches, and assigning said slice description data as one of said visual word classes.

12. The method of claim 11 comprising the processing platform, generating a histogram of the classified visual word classes, and calculating a similarity measure between the histogram and a plurality of reference histograms respectively associated with said reference slice description data in said memory device, and using said similarity measure as said comparison to identify said highest correlating slice description data.

13. The method of claim 11 comprising, said processing platform, classifying the image data portions into body material-related image data portions as a function of a Hounsfield value of the image data portions, and deleting, from said storage device, image data portions in patches that are unrelated to body material.

14. A method for storing an image data set comprising image data generated by a computed tomography scan of a plurality of slices of a body of a patient with respect to a body axis, said apparatus comprising:
 in a memory device, storing reference slice description data that represent a reference body other than the patient and that are organized in said memory according to reference body coordinates representing respective locations in said reference body along said body axis;
 in a processing platform, assigning slice description data to respective slices in the image data set according to a predetermined feature extraction technique, and executing a comparison between the slice description data and the reference slice description data to identify highest correlating reference slice description data in said memory device that have a highest statistical correlation to the slice description data respectively assigned to said slices in said image data set, and attaching respective reference body coordinate values to the respective slices in the image data set corresponding to locations along the body axis of the highest correlating reference slice description data;
 storing the image data set and the attached reference body coordinate values in a storage device; and
 said processing platform receiving a query for said image data set in the form of slice description data and converting the slice description data of the query into a reference body coordinate, and retrieving the image data set from the storage device by finding the reference body coordinate value attached to the image data set said storage device that corresponds to the reference body coordinate into which the query was converted.

15. A non-transitory computer-readable storage medium encoded with programming instructions, said storage medium being loaded into a computerized image data processing system and said programming instructions causing said computerized processing system to:
 access an image data set comprising image data generated by a computed tomography scan of a slice of a body of a patient with respect to a body axis;
 also access a memory device in which reference slice description data are stored that represent a reference body other than the patient and that are organized in said memory according to reference body coordinates representing respective locations in said reference body along said body axis;
 assign slice description data to the image data set according to a predetermined feature extraction technique, and execute a comparison between the slice description data and the reference slice description data to identify highest correlating reference slice description data in said memory device that have a highest statistical correlation to the slice description data assigned to said image data set, and attach a reference body coordinate value to the image data set corresponding to a location along the body axis of the highest correlating reference slice description data;
 store the image data set and the attached body coordinate value in a storage device; and
 receive a query for said image data set in the form of slice description data and convert the slice description data of the query into a reference body coordinate, and retrieve the image data set from the storage device by finding the reference body coordinate value attached to the image data set said storage device that corresponds to the reference body coordinate into which the query was converted.

16. A non-transitory computer-readable storage medium encoded with programming instructions, said storage medium being loaded into a computerized image data processing system and said programming instructions causing said computerized processing system to:
 access an image data set comprising image data generated by a computed tomography scan of a plurality of slices of a body of a patient with respect to a body axis;
 also access a memory device in which reference slice description data are stored that represent a reference body other than the patient and that are organized in said memory according to reference body coordinates representing respective locations in said reference body along said body axis;
 assign slice description data to respective slices in the image data set according to a predetermined feature extraction technique, and execute a comparison between the slice description data and the reference slice description data to identify highest correlating reference slice description data in said memory device that have a highest statistical correlation to the slice description data respectively assigned to said slices in said image data set, and attach respective reference body coordinate values to the respective slices in the image data set corresponding to locations along the body axis of the highest correlating reference slice description data;
 store the image data set and the attached body coordinate values in a storage device; and
 receive a query for said image data set in the form of slice description data and convert the slice description data of the query into a reference body coordinate, and retrieve the image data set from the storage device by finding the reference body coordinate value attached to the image data set said storage device that corresponds to the reference body coordinate into which the query was converted.

* * * * *